(12) United States Patent
Richardson

(10) Patent No.: US 9,492,314 B2
(45) Date of Patent: Nov. 15, 2016

(54) SYSTEM FOR ALTERING AND MAINTAINING TEMPERATURES OF OBJECTS

(75) Inventor: Michael P. Richardson, Anderson, SC (US)

(73) Assignee: Trailerlogic, LLC, Belton, SC (US)

(*) Notice: Subject to any disclaimer, the term of this patent is extended or adjusted under 35 U.S.C. 154(b) by 0 days.

(21) Appl. No.: 12/641,795

(22) Filed: Dec. 18, 2009

(65) Prior Publication Data

US 2011/0152982 A1 Jun. 23, 2011

(51) Int. Cl.
*A61F 7/00* (2006.01)
*A61F 7/02* (2006.01)

(52) U.S. Cl.
CPC .......... *A61F 7/02* (2013.01); *A61F 2007/0054* (2013.01); *A61F 2007/0096* (2013.01); *A61F 2007/0234* (2013.01)

(58) Field of Classification Search
CPC ............. A61F 7/02; A61F 2007/0234; A61F 2007/0096; A61F 2007/0054; F25D 17/02
USPC ........................................................ 607/104
See application file for complete search history.

(56) References Cited

U.S. PATENT DOCUMENTS

| | | |
|---|---|---|
| 311,764 A | 2/1885 | Johnson |
| 2,978,225 A | 4/1961 | Dallas, Jr. |
| 3,221,216 A | 11/1965 | Coleman, Jr. et al. |
| 3,916,911 A * | 11/1975 | Sauder et al. ............... 607/104 |
| 4,132,262 A | 1/1979 | Wibell |
| 4,149,541 A | 4/1979 | Gammons et al. |
| 4,691,762 A * | 9/1987 | Elkins et al. ................ 165/46 |
| 4,718,429 A * | 1/1988 | Smidt ........................... 607/104 |
| 4,998,415 A * | 3/1991 | Larsen ............................ 62/231 |
| 5,054,290 A | 10/1991 | Hogan |
| 5,241,951 A | 9/1993 | Mason et al. |
| 5,266,778 A * | 11/1993 | Bailey ............................ 219/497 |
| 5,363,663 A * | 11/1994 | Chen ................................ 62/99 |
| 5,433,083 A * | 7/1995 | Kuramarohit ................ 62/259.3 |

(Continued)

FOREIGN PATENT DOCUMENTS

| | | |
|---|---|---|
| CA | 2689678 A1 | 4/2008 |
| FR | 2059684 | 8/1970 |

(Continued)

OTHER PUBLICATIONS

Bernard et al., Treatment of Comatose Survivors of Out-of-Hospital Cardiac Arrest with Induced Hypothermia, Retrieved from the Interned: <URL:http://hypothermia.emcrit.org/hypoarts/bernard.pdf> (retrieved on Jan. 27, 2011).

(Continued)

*Primary Examiner* — Kaitlyn Smith
(74) *Attorney, Agent, or Firm* — Nelson Mullins Riley & Scarborough, LLP

(57) ABSTRACT

A system for altering or maintaining temperatures of objects having a heating/cooling unit having at least one primary fluid line for circulating a heating fluid, a cooling fluid or both through at least one pad in fluid communication with the heating/cooling unit. The heating/cooling unit may accommodate any number of primary fluid lines to correspond to the number of pads utilized or the heating/cooling unit may include at least one flow divider manifold in fluid communication with a primary fluid supply line for channeling a fluid through a plurality of pads.

8 Claims, 12 Drawing Sheets

(56) References Cited

U.S. PATENT DOCUMENTS

| | | | |
|---|---|---|---|
| 5,613,730 A | 3/1997 | Bluie et al. | |
| 5,659,933 A | 8/1997 | McWilliams | |
| 5,755,275 A * | 5/1998 | Rose et al. | 165/46 |
| 5,806,335 A | 9/1998 | Herbert et al. | |
| 5,924,181 A | 7/1999 | Takasugi | |
| 5,970,519 A * | 10/1999 | Weber | 2/81 |
| 6,009,713 A * | 1/2000 | Horn | 62/89 |
| 6,086,609 A * | 7/2000 | Buckley | 607/104 |
| 6,109,338 A * | 8/2000 | Butzer | 165/46 |
| 6,238,427 B1 * | 5/2001 | Matta | 607/104 |
| 6,349,412 B1 * | 2/2002 | Dean | 2/102 |
| 6,620,187 B2 * | 9/2003 | Carson et al. | 607/104 |
| 6,645,232 B2 * | 11/2003 | Carson | 607/104 |
| 6,660,027 B2 * | 12/2003 | Gruszecki et al. | 607/104 |
| 6,699,267 B2 * | 3/2004 | Voorhees et al. | 607/104 |
| 6,799,063 B2 * | 9/2004 | Carson | 600/372 |
| 6,802,855 B2 * | 10/2004 | Ellingboe et al. | 607/104 |
| 6,818,012 B2 * | 11/2004 | Ellingboe | 607/104 |
| 6,827,728 B2 * | 12/2004 | Ellingboe et al. | 607/104 |
| 6,942,015 B1 * | 9/2005 | Jenkins | 165/46 |
| 2002/0032473 A1 * | 3/2002 | Kushnir et al. | 607/104 |
| 2003/0176902 A1 * | 9/2003 | Gunn et al. | 607/104 |
| 2004/0030372 A1 * | 2/2004 | Ellingboe et al. | 607/104 |
| 2004/0030373 A1 * | 2/2004 | Ellingboe et al. | 607/104 |
| 2004/0159109 A1 * | 8/2004 | Harvie | 62/3.5 |
| 2004/0252918 A1 | 12/2004 | Yu et al. | |
| 2006/0048520 A1 | 3/2006 | Huang et al. | |
| 2006/0111765 A1 * | 5/2006 | Kirkman, Jr. | 607/104 |
| 2007/0085340 A1 | 4/2007 | Gammons | |
| 2007/0118194 A1 | 5/2007 | Mason et al. | |
| 2008/0058911 A1 * | 3/2008 | Parish et al. | 607/104 |
| 2008/0063771 A1 | 3/2008 | Dumm | |
| 2008/0307822 A1 | 12/2008 | Richardson | |
| 2009/0192421 A1 * | 7/2009 | Huster et al. | 601/44 |
| 2009/0240312 A1 * | 9/2009 | Koewler | 607/104 |
| 2009/0264969 A1 | 10/2009 | Gammons | |
| 2009/0308082 A1 * | 12/2009 | Monk | 62/3.3 |
| 2009/0312676 A1 * | 12/2009 | Rousso et al. | 601/15 |
| 2009/0312823 A1 * | 12/2009 | Patience et al. | 607/104 |
| 2010/0030306 A1 * | 2/2010 | Edelman et al. | 607/104 |
| 2010/0186435 A1 | 7/2010 | Vogel et al. | |
| 2011/0106023 A1 * | 5/2011 | Lowe | 604/291 |
| 2013/0090683 A1 * | 4/2013 | Schock | 606/203 |

FOREIGN PATENT DOCUMENTS

| | | |
|---|---|---|
| FR | 2539620 A1 | 7/1984 |
| GB | 2457627 A | 8/2009 |
| JP | 9253141 | 9/1997 |
| JP | 9286701 | 11/1997 |
| JP | 2006167418 | 6/2006 |
| JP | 2006-346428 | 12/2006 |
| WO | WO 97/24088 A1 | 7/1997 |
| WO | WO 98/23236 A1 | 6/1998 |
| WO | WO 2008/135710 A2 | 11/2008 |

OTHER PUBLICATIONS

PCT Invitation to Pay Additional Fees and, where applicable, protest fee, dated Dec. 17, 2010, for International Application No. PCT/US2010/048383.

PCT Notification of Transmittal of the International Search Report and the written opinion of the International Searching Authority, or the declaration, PCT International Search Report, PCT Written Opinion of the International Searching Authority, dated Feb. 17, 2011, for International Application No. PCT/US2010/060991.

Press Release, News & Publications entitled Cardiac Patient Saved Using Therapeutic Cooling, Albany Medical Center, Albany, NY, 2005-2007 News Archives at http://www.amc.edu/pr/PressRelease/01_13_09Th.html.

PCT International Preliminary Report on Patentability dated Jun. 19, 2012 issued in International Application No. PCT/US2010/060991.

PCT International Preliminary Report on Patentability and Written Opinion of the International Searching Authority for PCT Patent Application No. PCT/US2010/048383, Date of Report—Mar. 13, 2012.

* cited by examiner

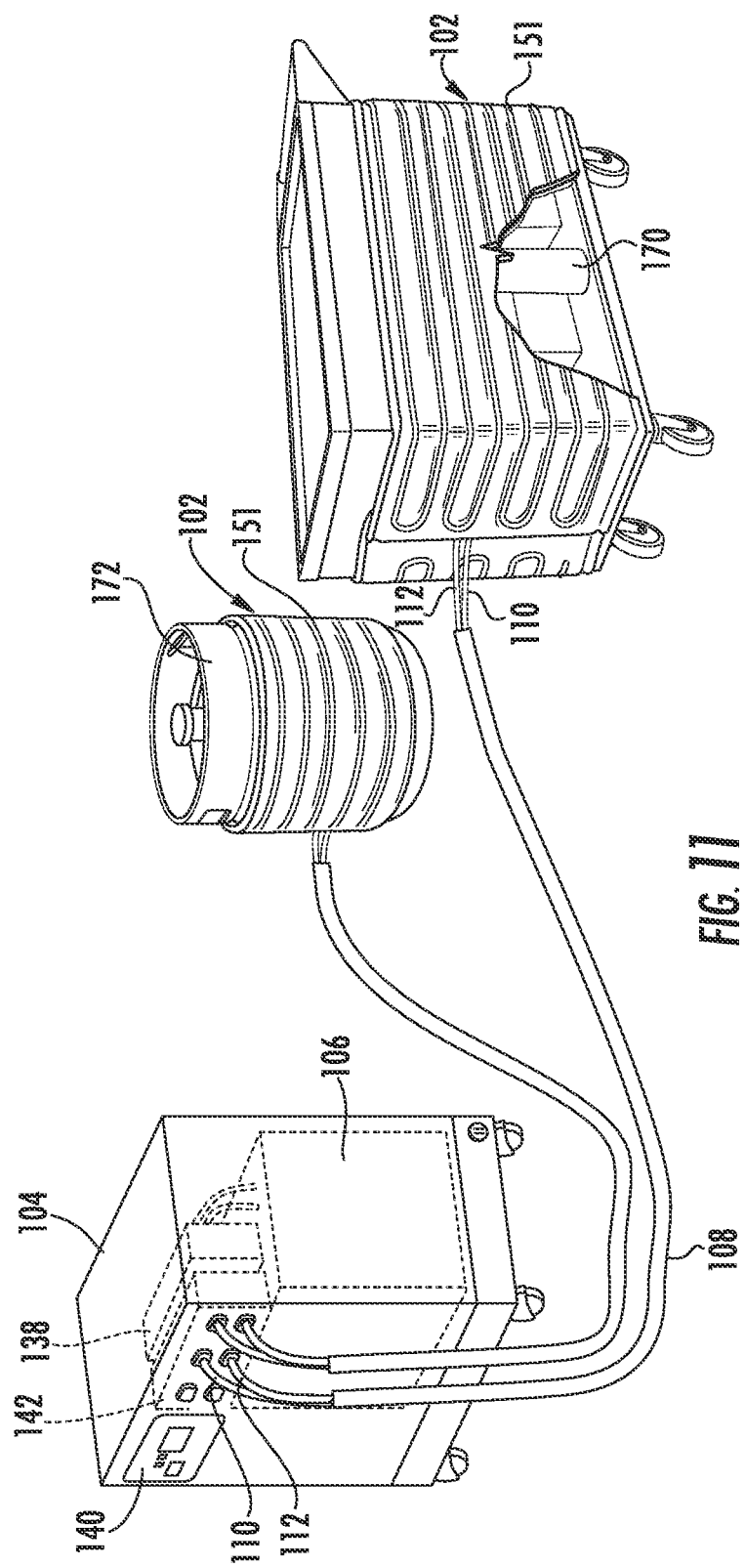

“SYSTEM FOR ALTERING AND MAINTAINING TEMPERATURES OF OBJECTS

FIELD OF THE INVENTION

The present invention relates to a system for altering or maintaining the temperature of an object.

SUMMARY OF THE INVENTION

One embodiment of the present invention is a system for maintaining or altering the temperature of objects. The system includes a heating/cooling unit with a fluid supply at a desired temperature, at least one primary fluid supply line and at least one primary fluid return line for providing fluid at a desired temperature for altering or maintaining the temperature of an object and circulating the fluid back to the heating/cooling unit for returning the fluid back to the desired temperature. The system further includes at least one pad that includes a first end and a second end, and an internal cavity that is segmented at the first end into a feed section and a return section. The pad further includes an inlet feed in fluid communication with the primary fluid supply line, located in the feed section and an outlet return in fluid communication with the primary fluid return line, located in the return section. The pad is configured to circulate fluid of a desired temperature from the feed section to the return section in a one-way flow arrangement. Further, the fluid of a desired temperature is circulated through the pad and is returned to the heating/cooling unit for returning the fluid to the desired temperature such that the fluid moves in a continuous cycle.

Another embodiment of the present invention is a system for maintaining or altering the temperature of objects. The system includes a heating/cooling unit with a fluid supply at a desired temperature, at least one primary fluid supply line and at least one primary fluid return line for providing fluid at a desired temperature for altering or maintaining the temperature of an object and circulating the fluid back to the heating/cooling unit for returning the fluid back to the desired temperature. The system further includes a pad including tubing in contact with the pad and spanning at least a portion of the pad and including a first end in fluid communication with the primary fluid supply line and a second end in fluid communication with the primary fluid return line. The pad is configured such that the fluid of a desired temperature enters the tubing through the first end and is circulated through the tubing and exits the second end and is returned to the heating/cooling unit for returning the fluid to the desired temperature such that the fluid moves in a continuous cycle.

The accompanying drawings which are incorporated in and constitute a part of this specification, illustrate one or more embodiments of the invention, and together with the description, serve to explain the principles of the invention.

BRIEF DESCRIPTION OF THE DRAWINGS

A full and enabling disclosure of the present invention, including the best mode thereof directed to one of ordinary skill in the art, is set forth in the specification, which refers to the appended drawings, in which:

FIG. 11 is a perspective view of a system for maintaining or altering the temperature of an object, wherein the pads are in direct contact with a food container and a beverage container, in accordance with an embodiment of the present invention.

Figure 1:
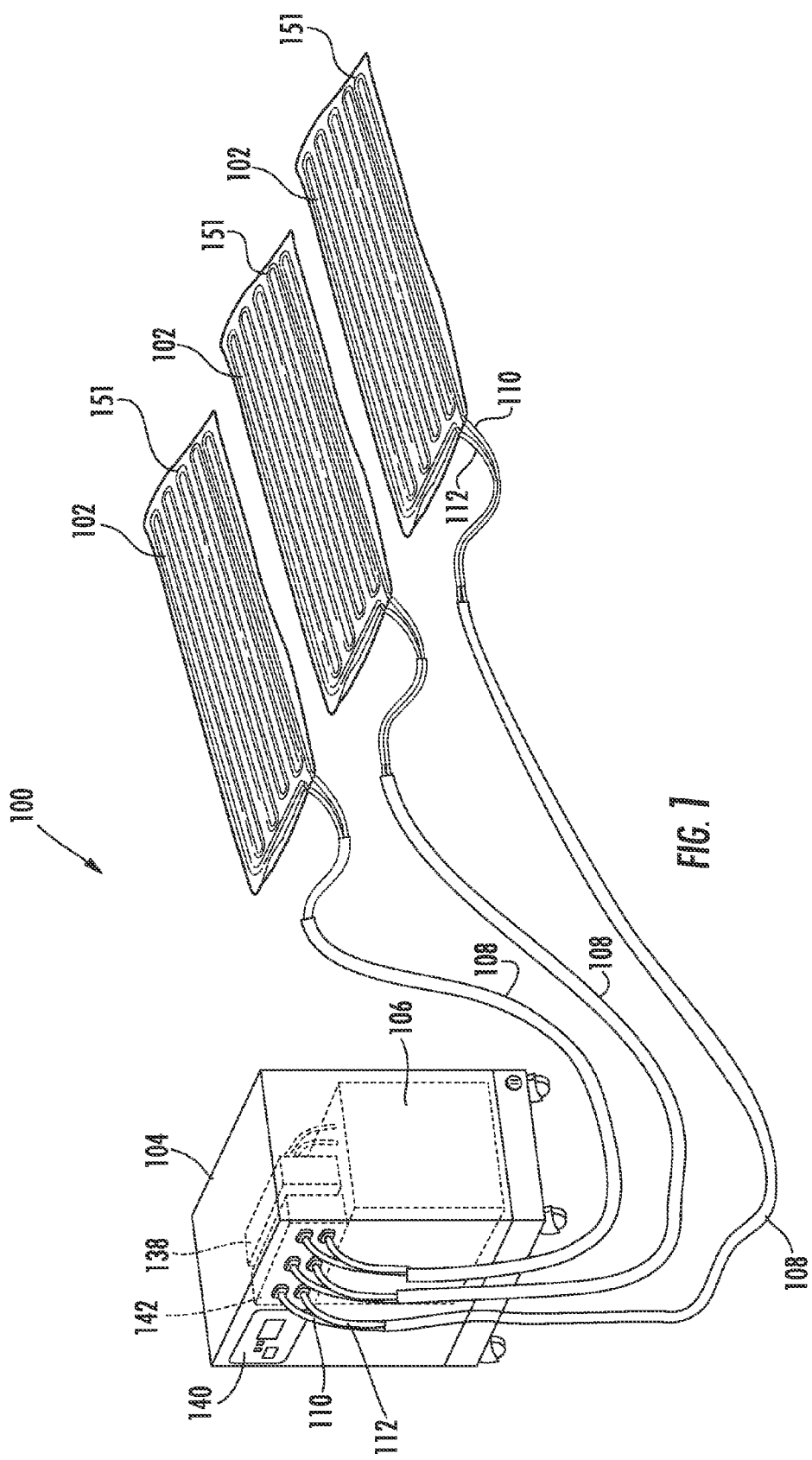
FIG. 1 is a perspective view of a system for maintaining or altering the temperature of an object in accordance with an embodiment of the present invention.

Repeat use of reference characters in the present specification and drawings is intended to represent same or analogous features or elements of the invention.

DETAILED DESCRIPTION OF THE INVENTION

Reference will now be made in detail to various embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

Referring to FIG. 1, a scalable system 100 for maintaining and altering temperatures of objects is shown. The objects that may be used in connection with the described invention can include both animate and inanimate objects as more fully discussed below. System 100 circulates a fluid at a desired temperature through a series of pads 102 to maintain or alter the temperature of an object that is in direct contact with pads 102. Based on the desired temperature of the object, system 100 may be altered to supply either warmed or chilled fluid. For example, if the object utilized with the invention is a food or beverage container that is to be chilled, system 100 may circulate fluid that ranges in temperatures from 35 to 45° F. Conversely, if the object utilized with the system is a food or beverage container that is to be warmed, system 100 may circulate fluid that ranges in temperatures from 150 to 200° F. The user's specifications will dictate the temperature of the fluid.

In the embodiment illustrated in FIG. 1, system 100 includes a heating/cooling unit 104 having a fluid container 106 for holding a fluid supply for circulating through pads 102. A primary fluid line 108, divided into a primary fluid supply line 110 and a primary fluid return line 110, extends from unit 104 for channeling fluid of a desired temperature to pads 102 and then circulating the fluid back to unit 104 for returning the fluid to the desired temperature.

In some embodiments, unit 104 may accommodate any number of primary fluid lines 108 to correspond to the number of pads 102 to be utilized with the present invention. For example, and as illustrated in FIG. 1, unit 104 may accommodate three primary fluid lines 108. In other embodiments, unit 104 may accommodate one, two, three, four, or more primary fluid lines 108.

Figure 2:
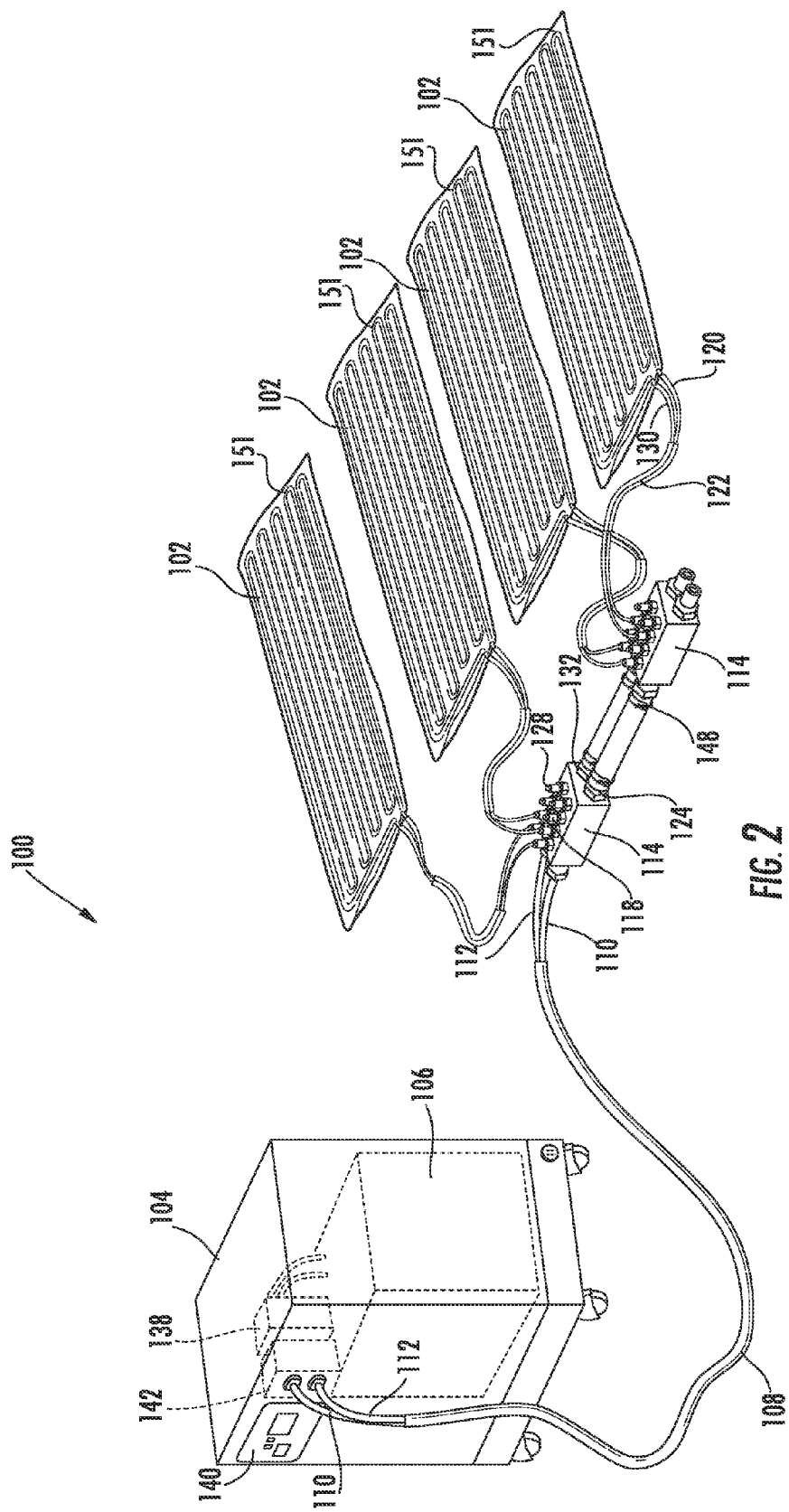
FIG. 2 is a perspective view of a system for maintaining or altering the temperature of an object where manifolds have been attached in accordance with an embodiment of the present invention.

In some embodiments, system 100 may be adapted to supply fluid to an even greater number of pads 102. In such embodiments and referring to FIGS. 2 and 3, at least one flow divider manifold 114 may be provided for channeling the inlet fluid through a plurality of pads 102. Flow divider manifold 114 includes a supply fluid input 116 connecting manifold 114 in fluid communication with primary fluid supply line 110. Supply fluid input 116 is further in fluid communication with at least one supply fluid output port 118 which is also in fluid communication with at least one secondary supply line 120 of a secondary fluid line 122 that provides fluid of a desired temperature to pads 102. In some embodiments, supply fluid input 116 may further be in fluid communication with supply fluid manifold port 124 when more than one manifold 114 is utilized as shown in FIG. 2.

Flow divider manifold 114 also includes a return fluid output 126 connecting manifold 114 in fluid communication with primary fluid return line 112. Return fluid output 126 is also in fluid communication with return fluid input ports 128 which are in further fluid communication with secondary return line 130 of secondary fluid line 122, for returning fluid that has exited pads 102. In some embodiments, return fluid output 126 may also be in fluid communication with return fluid manifold port 132 when more than one manifold is utilized as shown in FIG. 2.

In embodiments where manifolds are utilized, at least one pad 102 is provided in direct fluid communication with secondary supply line 120 for receiving the fluid of a desired temperature from heating/cooling unit 104. The pad 102 is also connected in direct fluid communication with secondary return line 130 for returning fluid to heating/cooling unit 104. Accordingly, pad 102 may be adapted to system 100 such that fluid of a desired temperature may be circulated through pad 102 and then fluid may be returned to unit 104 for returning the fluid to the desired temperature. The recirculation of fluids helps to maintain the temperature of pad 102 and the object with which pad 102 makes direct contact.

Figure 4:
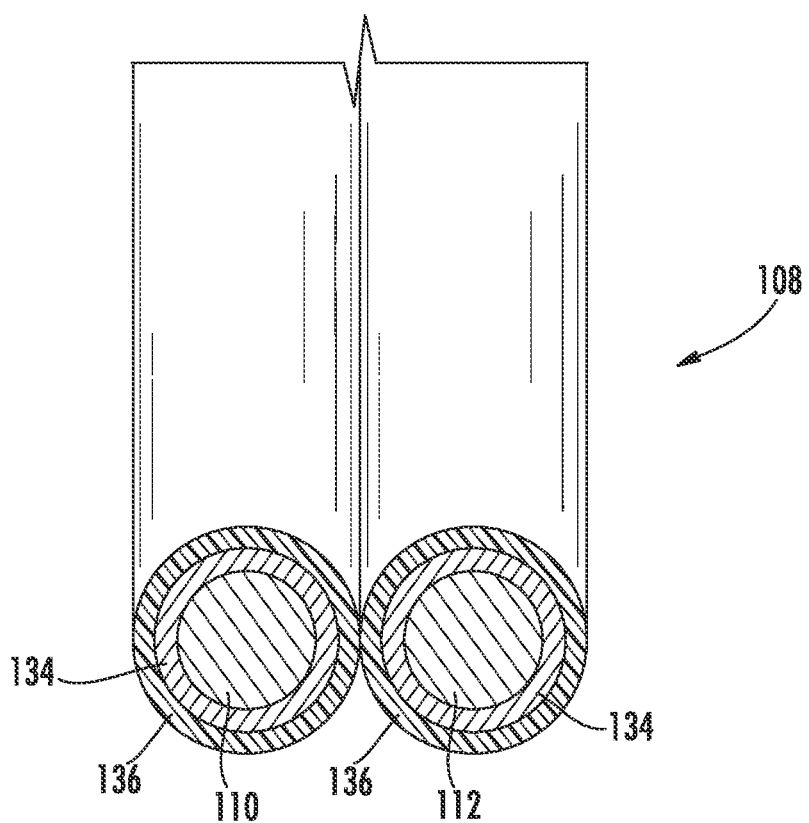
FIG. 4 is a cross-sectional view of a primary fluid line in accordance with an embodiment of the present invention.

In order to maintain the temperatures of the fluids within the lines and to avoid any substantial damage to the lines, primary fluid line 108 may be constructed as shown in FIG. 4. Primary fluid line 108 includes primary supply line 110 and primary return line 112 which are surrounded by an insulation layer 134 that is covered by a wear resistant layer 136. Primary supply line 110 and primary return line 112 may be constructed, in some embodiments, of a polyvinyl chloride hose. Insulation layer 134 may be constructed of any material known in the art that will maintain the necessary temperature of the fluid in primary supply line 110. In some embodiments, insulation layer 134 may be made of a closed cell extruded foam, including polyisocyanurate or polyurethane. Wear resistant layer 136 may be made of any material known in the art for maintaining the integrity of the lines, for example an extruded PVC may be used as wear resistant layer 136.

Primary fluid line 108 may also be constructed such that primary supply line 110 and primary return line 112 are releaseably connected and may be separated, so that the lines may properly enter different components of manifold 114 and/or unit 104, while still maintaining the insulation layer 134 and the wear resistant layer 136. Although FIG. 4 makes reference to primary fluid line 108, secondary fluid line 122 may be constructed in the same or similar manner and house secondary supply line 120 and secondary return line 130 with an insulation layer and a wear resistant layer.

In some embodiments, and as illustrated in FIG. 1, a fluid pump 138 may be included in unit 104 which pressurizes the system and forces the fluid through the supply lines and into pads 102, and circulates that fluid back to unit 104 for returning the fluid to a desired temperature. In some embodiments, pump 138 includes a stepping motor for adapting to changes in fluid level as pads 102 are added or removed from unit 104 or manifold 114. In some embodiments, system 100 may be designed to hold sufficient fluid to support 28 pads with a 25 gallon fluid container in unit 104.

Figure 5:
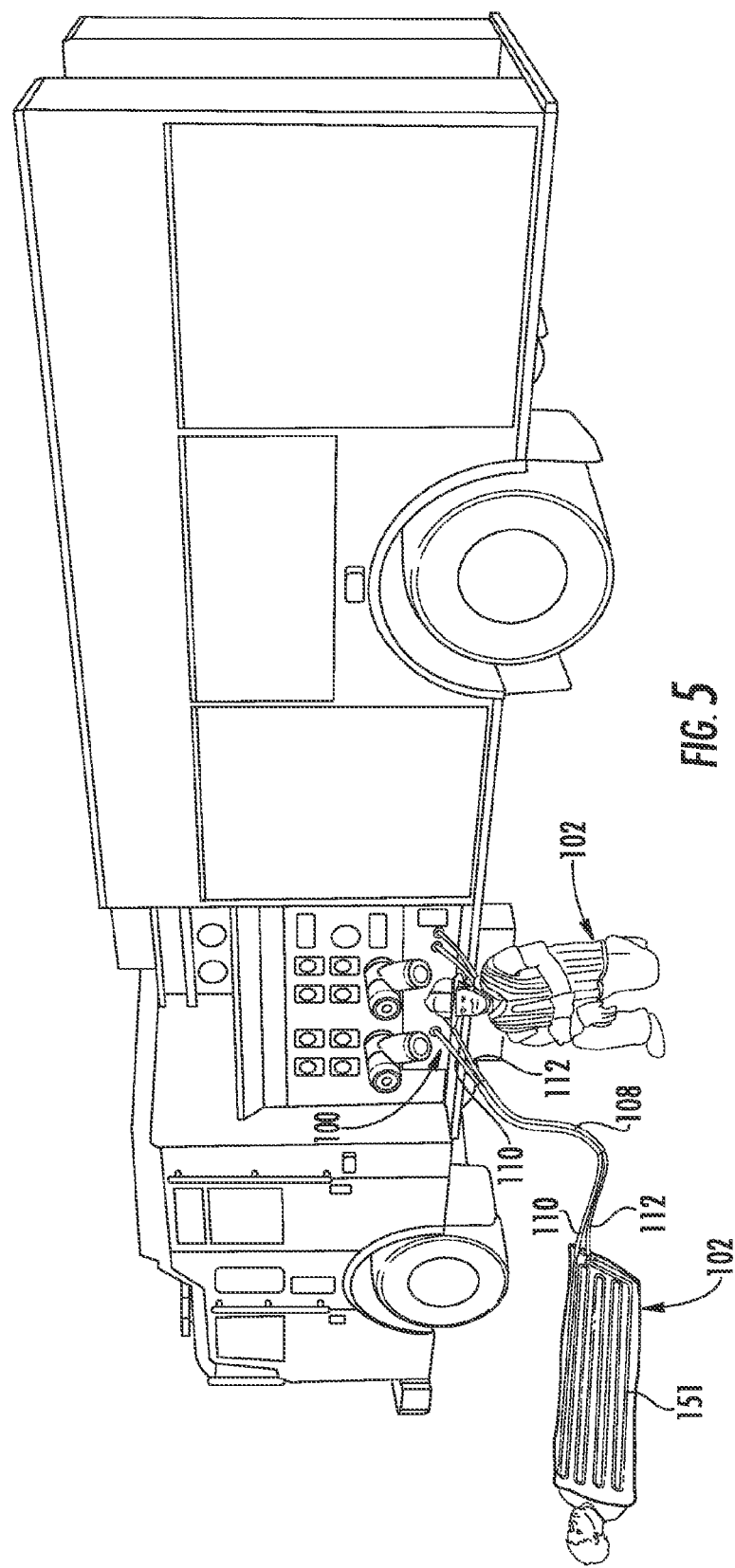
FIG. 5 is a perspective view of a system for maintaining or altering the temperature of an object adapted to a fire truck in accordance with an embodiment of the present invention.

Heating/cooling unit 104 may connect to ground-based power or may be adapted to a vehicle and may rely on the power generated from the vehicle as shown in FIG. 5. In other embodiments, due to the limited power demands of system 100, it may run on portable power generator units or batteries. For example, in some embodiments, system 100 may connect to a lithium-ion battery that supplies between 10 and 32 volts of electricity to power heating/cooling unit 104.

In an embodiment, unit 104 includes a heater and a cooling valve to control the temperature of the fluid between the ranges of 30 and 250° F. A unit of the type manufactured by Advantage Engineering, Inc. 525 East Stop 18 Road, Greenwood, Ind. 46142, can serve to heat or cool the fluid to the desired temperature and then circulate the fluid through a plurality of pads 102. In some embodiments, the fluid may be a glycol and water solution or other similar fluid to prevent freezing when unit 104 is to provide chilled fluid. Such fluids may be utilized to maintain circulation of the fluid through the various supply lines and manifolds. In a particular embodiment, the chilled fluid includes approximately 30% by volume of glycol to prevent freezing. In embodiments where unit 104 is utilized to provide heated fluid, unit 104 may include a pressure increasing valve (not shown) for increasing the pressure of the fluid to ensure the fluid does not enter a gaseous phase.

In further embodiments, unit 104 may include a temperature sensor and pressure display 140 operatively associated with the fluid for monitoring the temperature of the fluid as it leaves unit 104 for circulation through pads 102, as well as the pressure of the fluid in the lines. Temperature sensor and pressure sensor 140 may also be operatively associated with unit 104 such that when the temperature of the supply fluid falls outside of a desired range, unit 104 may adjust the heating or cooling mechanism to provide fluid at the appropriate temperature.

In some embodiments, unit 104 may be adapted to include an outlet pressure reducing valve 142 in fluid communication with primary fluid supply line 110 for creating a low flow pressure of the supply fluid through the system 100. The low flow pressure of the supply fluid through primary fluid supply line 110 may be approximately 10 psi in an embodiment. In a further embodiment, primary fluid supply line 110 and primary fluid return line 112 may be approximately 1 inch in diameter for maintaining flow volume and pressure to flow divider manifold 114 or pads 102 under the low flow pressure condition of the system. Further, in some embodiments, secondary supply and return lines 120 and 130 may be approximately 3/8 inch in diameter for maintaining pressure and flow volume to circulate the fluid through pad 102.

Figure 6:
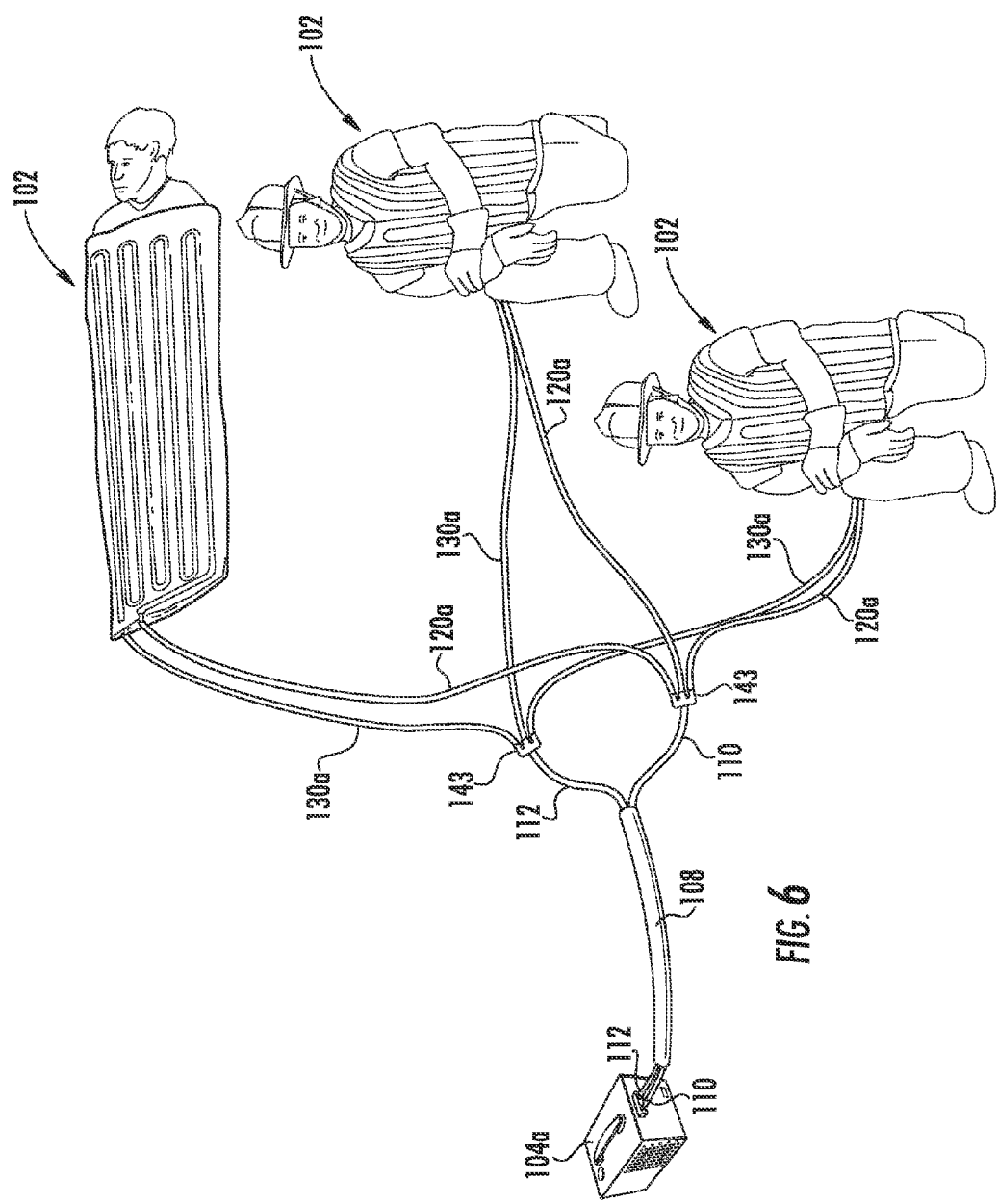
FIG. 6 is a perspective view of a handheld system for altering or maintaining the temperature of an object in accordance with an additional embodiment of the present invention.

In an additional embodiment, unit 104a may be handheld for additional mobility of system 100 as shown in FIG. 6. In such embodiments, unit 104a may include a refrigeration circuit to cool the temperature of the fluid to between about 45 and 85° F. In further embodiments, unit 104a may cool the temperature of the fluid to between about 60 and 78° F. As discussed above, unit 104a may connect to ground power or a battery. In some embodiments, unit 104a may connect to a 24V battery from a vehicle or a portable 24V lithium ion battery. Unit 104a may also include a container (not shown) for supplying fluid to pads 102. In some embodiments, the container of unit 104a may be of sufficient size to contain between about 1 to 50 ounces of fluid. In other embodiments, the container of unit 104a may be of sufficient size to contain between about 2 to 25 ounces of fluid.

In some embodiments, and as shown in FIG. 6, unit 104a may accommodate more than one pad 102 to maintain or alter the temperature of the object in contact with pads 102. In such embodiments, a flow divider 143 may be utilized to provide fluid communication to primary fluid supply line 110 and primary fluid return line 112 with each pad 102. In embodiments of the invention when a flow divider 143 is utilized, a secondary supply line 120a and a secondary return line 130a may be utilized in direct fluid communication with pads 102. Although flow divider 143 is shown in connection with unit 104a, it may also be utilized with unit 104 in the same or similar manner to accommodate one or more pads 102.

Heating/cooling unit 104 may be constructed to allow for connection and disconnection of pads 102 without having to shutdown system 100. In some embodiments, secondary fluid supply line 120 and secondary fluid return line 130 are connected to flow divider manifold 114 using a quick connect coupling so that the supply and return lines may be connected and disconnected without turning off unit 104 or having to use tools to complete the connections.

Figure 3:
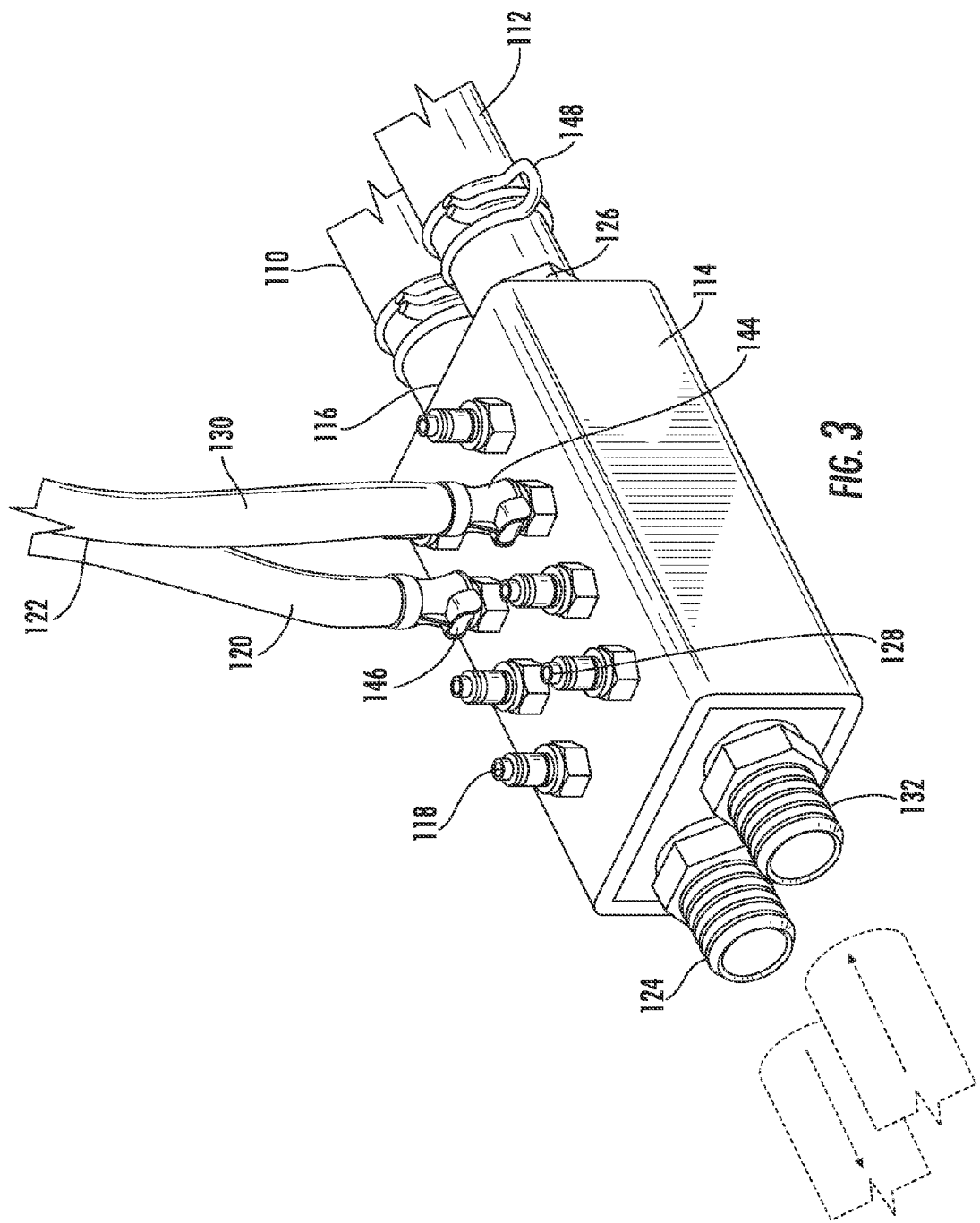
FIG. 3 is a perspective view of a flow divider manifold in accordance with an embodiment of the present invention.

Referring to FIG. 3, quick connect couplings 144 are shown on secondary supply line 120 and secondary return line 130 for connecting with the complementary ports of manifold 114. Although FIG. 3 illustrates quick connect couplings on manifold 114, such couplings may also be utilized on the primary supply and return lines 110 and 112 connected to unit 104. Quick connect couplings 144 include an internal lock, that when quick connect couplings 144 are properly situated over and pressed down on the complementary ports, couplings 144 are locked into fluid communication with either supply fluid input 116 or supply fluid output 118. Quick connect couplings 144 may be removed by actuating release 146, and removing coupling 144 from the complementary port. When quick connect couplings 144 are removed from a complementary port, a check valve (not shown) in the quick connect coupling 144 is closed to prevent fluid from leaking out of either secondary supply line 120 or secondary return line 130. Although the invention is described using the particular quick connect coupling described above, those of ordinary skill in the art will recognize that other quick connect couplings, which produce the same or similar results, may be used in additional embodiments.

As shown in FIG. 2, a plurality of flow divider manifolds 114 may be arranged in order to scale the system to the number of pads 102 required by the user. Each manifold 114 is connected such that each supply fluid input 116 of each manifold 114 is in fluid communication with primary fluid supply line 110 and each return fluid output 126 is in fluid communication with primary return line 112. In some embodiments, and, as shown in FIG. 2, lines are connected to manifolds 114 by being placed over ports of manifold 114 and held in place with the use of a hose clamp 148. In other embodiments, the connections between the lines and manifolds are accomplished using common quick connect couplings as described above.

Figure 7:
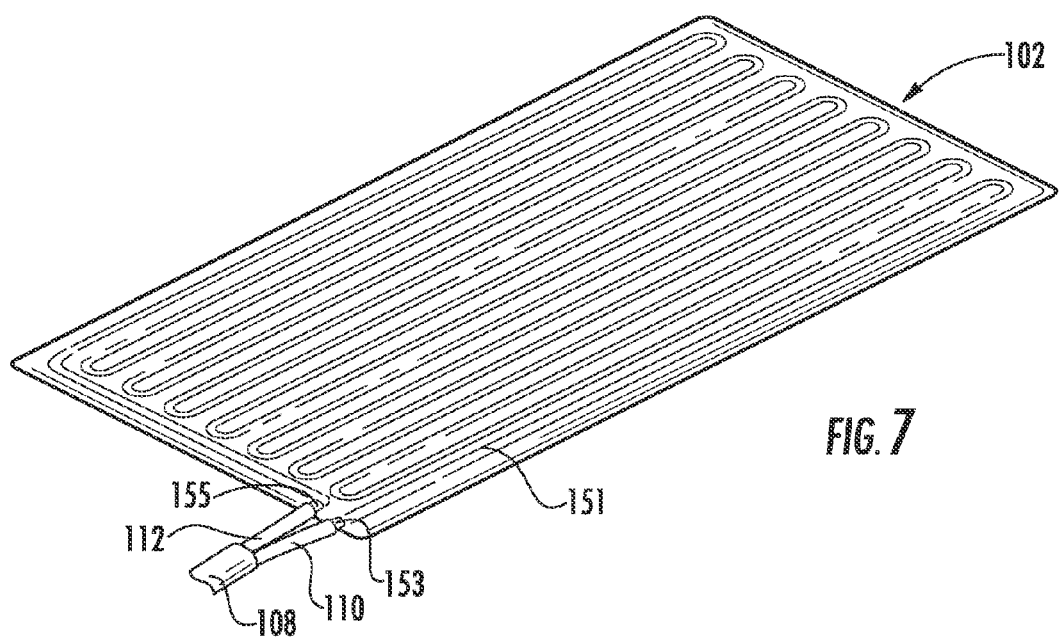
FIG. 7 is a perspective view of a pad in accordance with an embodiment of the present invention.

Referring to FIG. 7, an embodiment of pad 102 is shown connected in fluid communication with primary fluid line 108, which is divided into primary supply line 110 and primary return line 112 as it reaches pad 102. As the fluid of a desired temperature enters pad 102 through primary fluid supply line 110, the fluid is circulated around pad 102 and back to heating/cooling unit 104 through primary fluid return line 112 so that the object in contact with pad 102 is maintained at a desired temperature through direct contact. Although not illustrated, when a manifold 114 is utilized with system 100, secondary fluid line 122, which is divided into secondary supply line 120 and secondary return line 130 may connect to pad 102 in a similar manner as primary fluid line 108.

In an embodiment of the present invention, pad 102 includes tubing 151 for properly dispersing fluid of a desired temperature throughout pad 102. As shown in FIG. 7, tubing 151 may sufficiently cover an area of pad 102 to ensure the temperature of the object in contact with pad 102 is altered or maintained as desired. In such embodiments, tubing 151 connects to primary fluid supply line 110 at a first end 153 and at a second end 155 connects to primary fluid return line 112. Such a configuration allows the fluid of a desired temperature to enter tubing 151, travel through tubing 151 from first end 153 to second end 155, and be returned to heating/cooling unit 104 for returning the fluid to the desired temperature.

Tubing 151 may be made of any material known in the art that can withstand the temperature of the fluid in tubing 151. In some embodiments, tubing 151 is constructed of polyethylene or polyurethane. The use of system 100 will dictate the required materials used to construct tubing 151.

Tubing 151 may also be of any diameter sufficient to allow fluid to circulate from first end 153 to second end 155. For example, in some embodiments, tubing 151 may have a diameter between about 1/64 inch and about 1 inch. In other embodiments, tubing 151 may have a diameter of between about 1/32 inch and about 1/8 inch. Again, the particular use of system 151 will dictate the necessary size of tubing 151.

Figure 8:
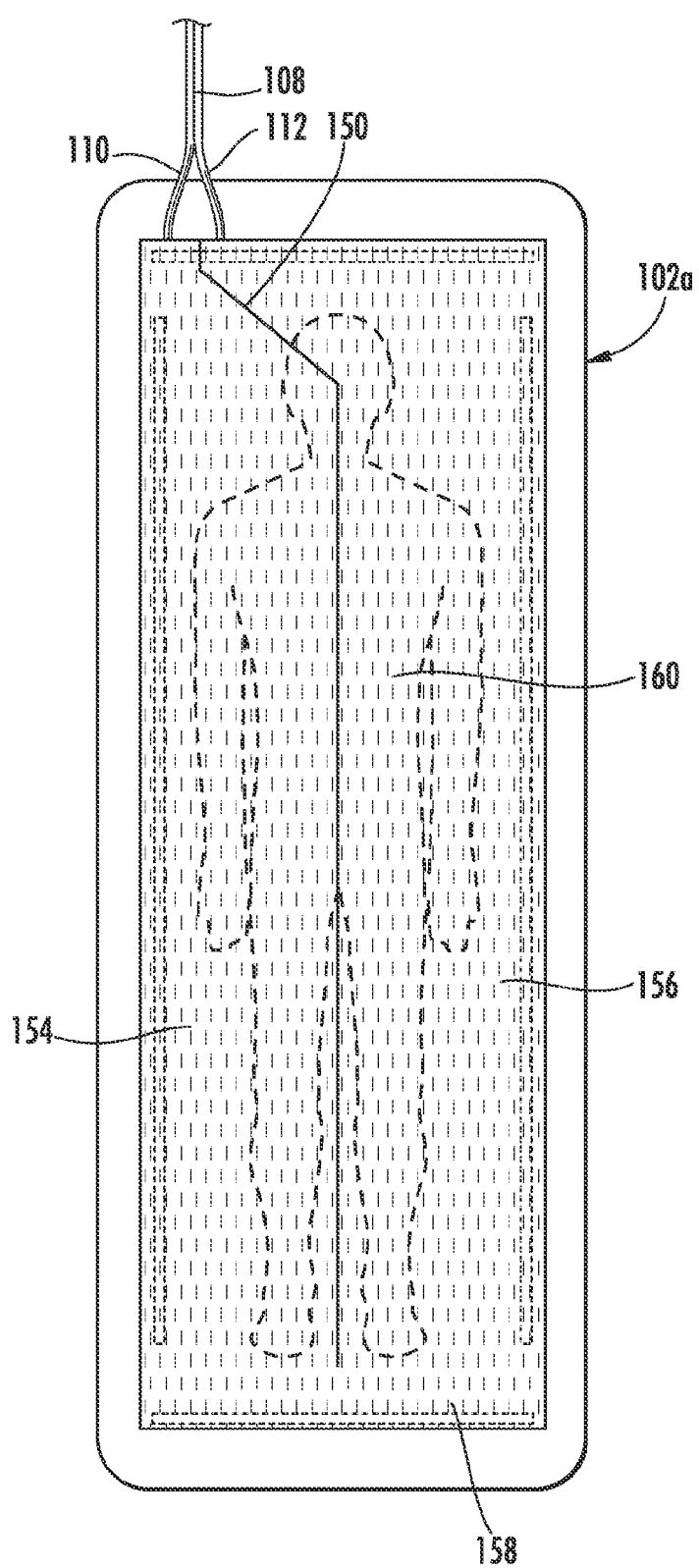
FIG. 8 is a top view of a pad placed over a human in accordance with an additional embodiment of the present invention.
Figure 9:
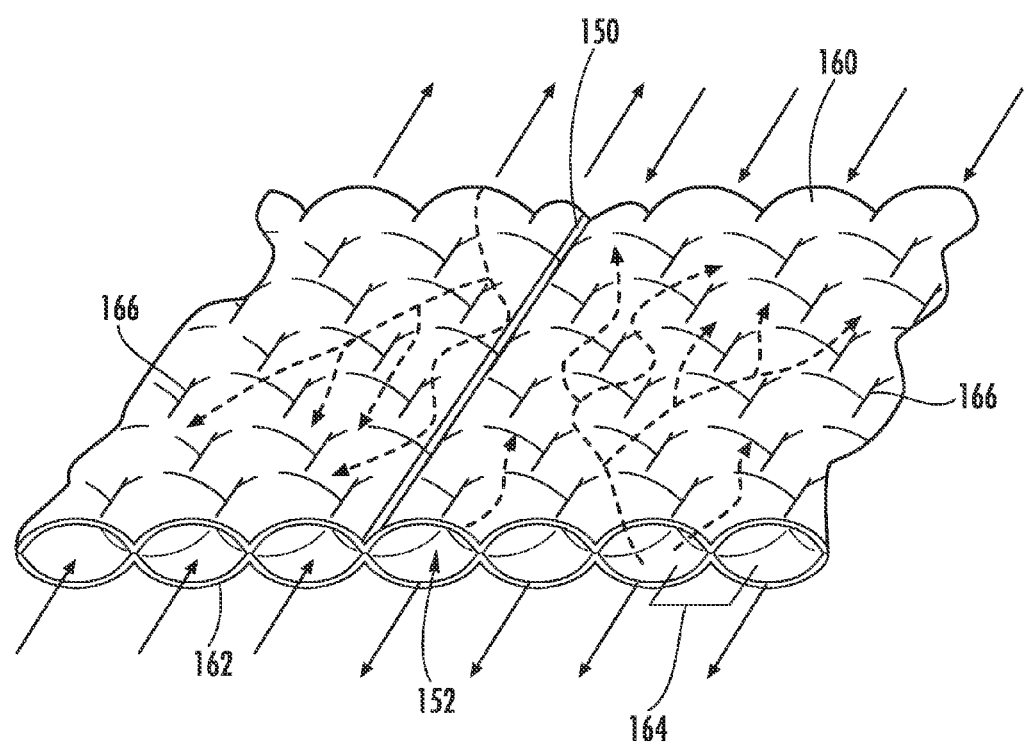
FIG. 9 is a cross-sectional perspective view of a section of the pad shown in FIG. 8 in accordance with an additional embodiment of the present invention.

Referring now to FIGS. 8 and 9, an additional embodiment of pad 102a is illustrated. Pad 102a includes a flow director 150 segmenting an interior fluid cavity 152 in pad 102a into a feed section 154 in fluid communication with primary fluid supply line 110 and a return section 156 in fluid communication with primary fluid return line 112. Such a configuration allows the fluid of a desired temperature to circulate first through feed section 154 and then into return section 156 in a consecutive one-way flow arrangement. An opening at distal end 158 of cooling pad 102a is provided in flow director 150 so that fluid can pass from feed section 154 into return section 156. As shown in FIG. 9, flow director 150 may be formed by heat welding a top side 160 of cooling pad 102a to a bottom side 162 so that fluid cannot pass through flow director 150.

In a further embodiment and as shown in FIG. 9, interior fluid cavity 152 of cooling pad 102a may include a plurality of fluid dispersion cells 164 for directing fluid of a desired temperature throughout feed section 154 and return section 156. Fluid dispersion cells 164 may be formed by heat welding, as indicated by reference number 166, top side 160 and bottom side 162 of pad 102a in a staggered arrangement.

Due to the capabilities of system 100, the present invention may be utilized in connection with a number of different objects in various applications. For example, the present invention can be utilized with both animate and inanimate objects and adapted for use in the fields of sports, entertainment, military, rescue, and others.

In particular, the present invention may provide chilled fluid in order to lower the core temperature of a human or animal that has overheated or is on the verge of overheating. For example, in the field of sports, members of pit crews of automobile racing teams routinely become overheated as a result of the layers of clothing that must be worn, the heat of the sun, and their proximity to a number of running mechanical parts. In such instances, the members of the pit crew may be cooled by the direct contact of pads 102 of system 100 of the present invention. Similarly, firefighters or victims who have come in close contact with fire may also use the present invention to lower their core body temperature through the direct contact with pads 102. In such situations, and as discussed above, the portability of system 100 allows for the present invention to be adapted to vehicles (shown in FIG. 5) to better address situations in the field, like at the spot of a fire, rather than be limited to a confined area.

With respect to rescue operations, cooling of a human's core temperature may also be beneficial to victims of other medical disorders. For example, studies have indicated that cooling the core temperature of a victim of a stroke or cardiac arrest to near hypothermic state may limit the amount of brain damage suffered by the victim. Accordingly, in some embodiments, such victims may have their core body temperatures lowered through direct contact with pads 102, circulating a fluid between about 55 and 80° F., of a mobile system 100 or a system 100 that is located in an ambulatory vehicle. The mobility of system 100 may allow the victim to take advantage of immediate aid prior to arriving at a hospital where greater care can be administered.

In contrast to the above described scenarios, system 100 may also supply warmed fluid to increase the core body temperature of a human, if desired. For example, the core body temperature of a victim of hypothermia needs to be increased to ensure normal body function. In such scenarios, a victim may warm their body temperature through the direct contact with a warmed pad 102 of system 100 until more help can be obtained or their body temperature has reached an appropriate level.

Figure 10A:
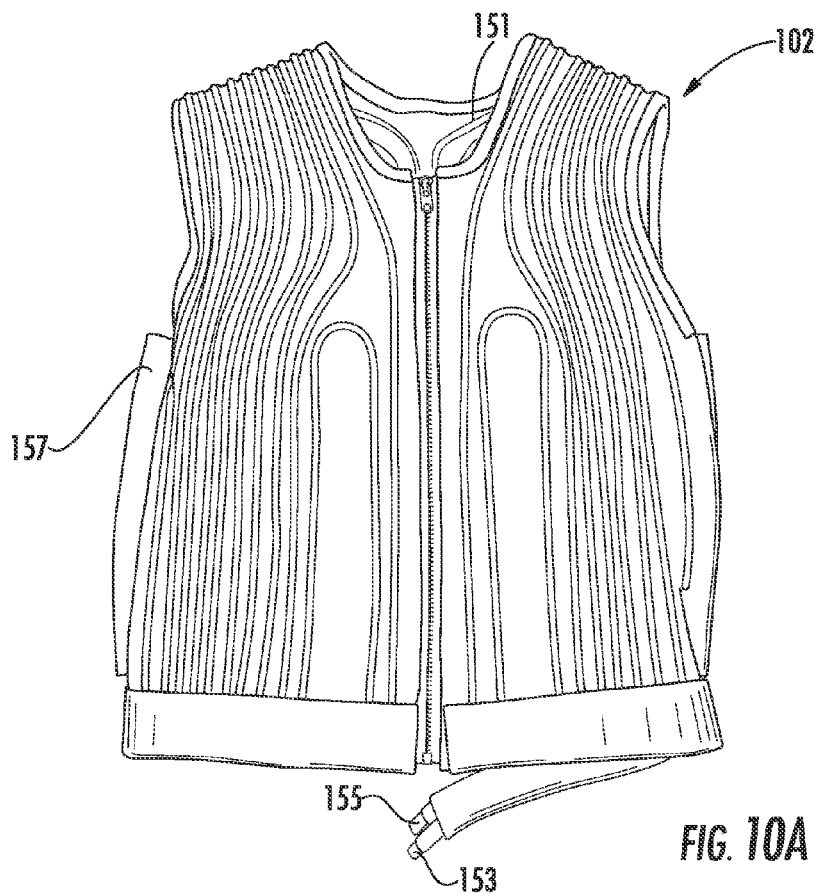
FIG. 10A is a front view of a pad configured as a vest, where the vest is zipped, in accordance with an embodiment of the present invention.
Figure 10B:
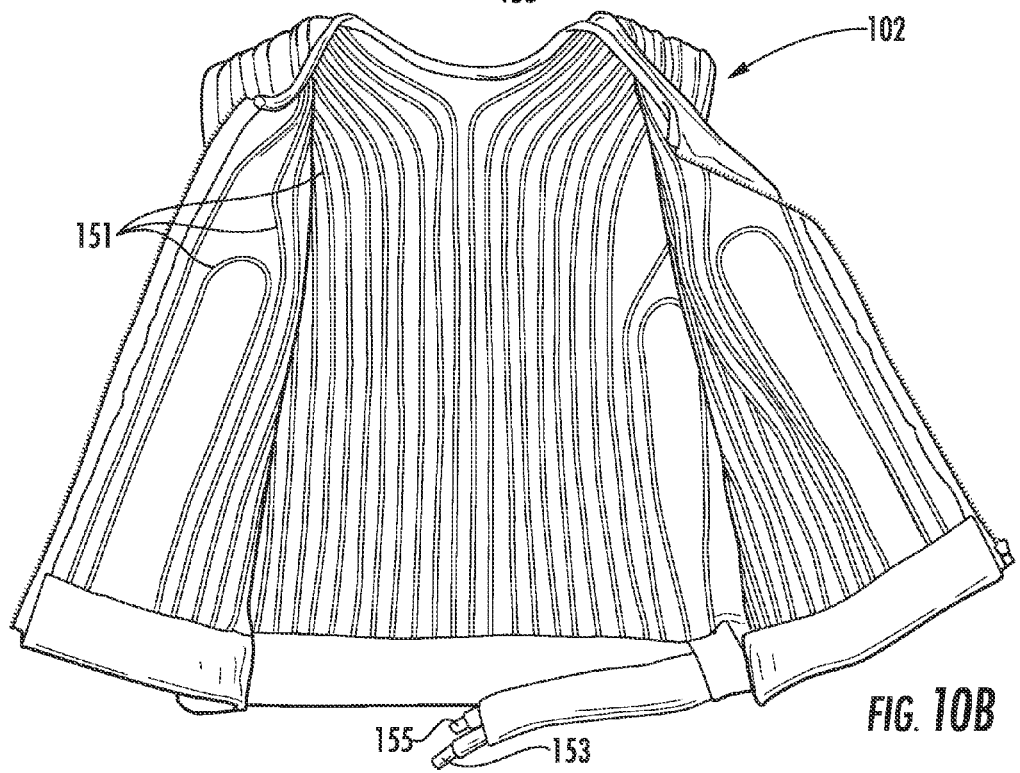
FIG. 10B is a front view of a pad configured as a vest, where the vest is unzipped, in accordance with an embodiment of the present invention.

In embodiments where pad 102 is contacted with a human, pad 102 may be constructed in any manner to ensure the most effective contact. For example, as shown in FIGS. 1 and 2, pad 102 may be configured with a rectangular or other polygonal shape. In other embodiments, as seen in FIGS. 10A and 10B, pad 102 may be in the shape of a vest to ensure sufficient contact is made with a person's chest and back. The vest shape of pad 102 may also allow the user to easily and quickly put pad 102 in direct contact with a person in times of immediate need. Also, as shown in the Figures, tubing 151 may be placed on a particular side of pad 102 to ensure sufficient contact is made with the object.

Figure 10C:
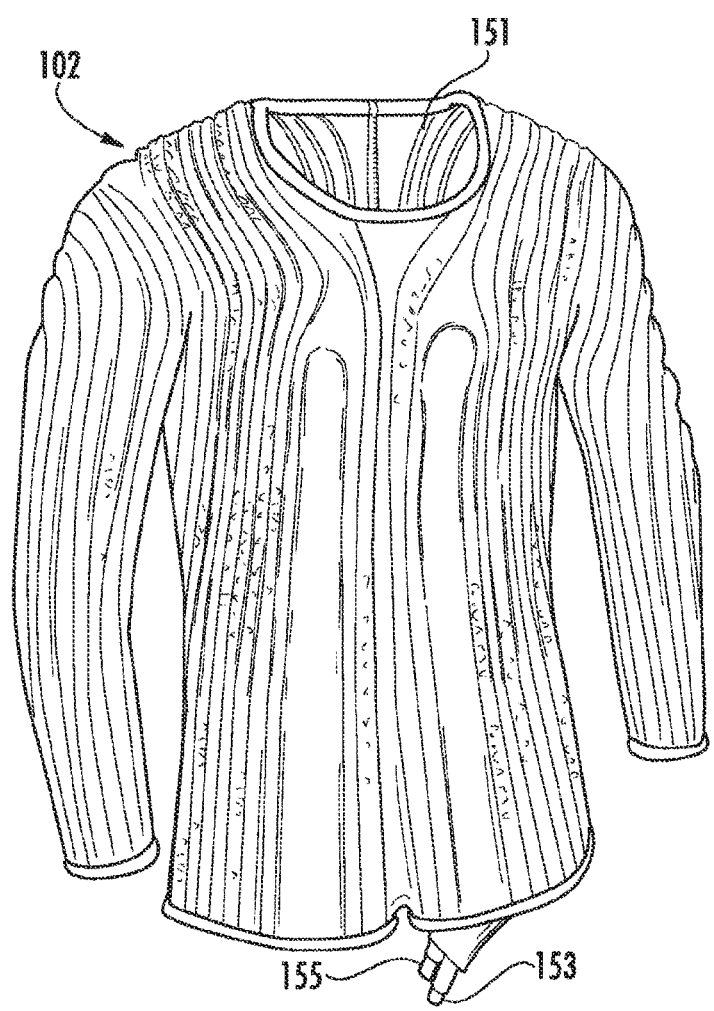
FIG. 10C is a front view of a pad configured as a unitard in accordance with an embodiment of the present invention.

In other embodiments, pad 102 may be configured in the shape of a unitard (as shown in FIG. 10C) or a leotard. Such configurations may allow for pad 102 to contact the arms or the groin area if these are necessary for the particular application. Pads 102 may also be fitted within a person's clothing to aid in altering or maintaining the temperature of a person. For example, a football player's jersey may be outfitted with a pad 102 such that when the player is not directly participating in the sport, he may insert a primary or secondary fluid line into pad 102 and connect to tubing 151 such that system 100 can provide warmed or cooled fluid, depending on the situation.

Pads 102 may also include other material to ensure sufficient contact. For example, and as shown in FIGS. 10A and 10B, when pad 102 is in the shape of a vest, the vest may include compression material 157 to connect the front and back sides of the vest. The compression material 157 may aid in maintaining the direct contact of pad 102 with the person. In other embodiments, pads 102 may include materials that extend from either end of pad 102 such that the materials may be fastened or tied together to ensure proper placement and fitting to an object.

Although the invention has been described with reference to humans, system 100 may also be utilized with animals. For example, the present invention may prove beneficial in attempting to reduce the core temperature of animals, including horses or dogs that participate in racing or other events. In such instances, the animals may lie on a pad 102 or a pad 102 may be configured to fit a particular animal.

In other embodiments, system 100 may be utilized with inanimate objects including food and beverage items. For example and as shown in FIG. 11, containers 168 of food 170 that need to be cooled can be maintained at desired temperatures by the direct contact with pads 102. As shown in FIG. 11, pad 102 may be wrapped around a container 168 such that the container 168 and contents inside maintain a desired temperature. In a similar manner, pads 102 may also be wrapped around beverage containers, for example beer kegs 172, as shown in FIG. 11, for maintaining the beverage at a desired temperature.

System 100 may also be utilized in maintaining or altering the temperature of items for medical use. For example, system 100 may maintain a container of drugs or blood in contact with pads 102 at a particular temperature to avoid spoliation. Such methods may prove beneficial in large casualty situations in that supplies may be sent to the disaster site and may be properly maintained to help those affected by the disaster.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole and in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

The invention claimed is:

1. A system for maintaining or altering the temperature of an object, the system comprising:
   a heating/cooling unit capable of supplying a heating fluid, a cooling fluid, or both;
   a heating fluid and a cooling fluid and comprising a fluid supply;
   a single primary fluid supply line extending from the heating/cooling unit; and
   a single primary fluid return line extending from the heating/cooling unit; the single primary fluid supply line and the single primary fluid return line in fluid communication with the fluid supply for providing fluid at a desired temperature for altering or maintaining the temperature of the object and circulating the fluid back to the heating/cooling unit for returning the fluid back to the desired temperature;
   a plurality of pads, each of the plurality of pads comprising:
      a first pad end and a second pad end, and a pad area between the first pad end and the second pad end;
   tubing in contact with a portion of the pad area, the tubing comprising:
      a first tubing end of one of the plurality of pads in fluid communication with the single primary fluid supply line; and
      a second tubing end of one of the plurality of pads in fluid communication with the single primary fluid return line;
   a flow divider manifold independent of and spaced from both the heating/cooling unit and the object and comprising a supply fluid input, a series of supply fluid output ports in fluid communication with the single primary fluid supply line for receiving and dispersing the fluid at the desired temperature, a return fluid output, and a series of return fluid input ports in fluid communication with the single primary fluid return line for returning the fluid;
   at least one secondary fluid line comprising:
      a secondary fluid supply line in fluid communication with one of the supply fluid output ports and in direct fluid communication with the first tubing end, and a secondary fluid return line in communication with one of the return fluid input ports and in direct fluid communication with the second tubing end; and
   wherein the system is configured to continuously supply a fluid at the desired temperature to the first tubing end and circulate the fluid through the tubing before exiting the second tubing end and returning the fluid to the heating/cooling unit so that the temperature of the fluid can be altered or maintained at the desired temperature before returning the fluid to the single primary fluid supply line.

2. The system of claim 1 further comprising at least one additional flow divider manifold independent of and spaced from both the heating/cooling unit and the object and comprising a supply fluid input, a series of supply fluid output ports in fluid communication with the single primary fluid supply line for receiving and dispersing the fluid at the desired temperature, a return fluid output, and a series of return fluid input ports in fluid communication with the single primary fluid return line for returning the fluid.

3. The system of claim 1, wherein the pad is configured as a vest.

4. The system of claim 1, wherein the pad is configured in a polygonal shape.

5. The system of claim 1, wherein the system is configured to be mounted to a vehicle and utilizes the vehicle's source of electricity.

6. The system of claim 1, wherein the system is handheld.

7. The system of claim 1, wherein the supply fluid output ports and return fluid inlet ports comprise releasable connections.

8. The system of claim 2, wherein the supply fluid output ports and return fluid inlet ports of the flow divider manifold and the at least one additional flow divider manifold comprise releasable connections.

* * * * *

UNITED STATES PATENT AND TRADEMARK OFFICE
CERTIFICATE OF CORRECTION

PATENT NO. : 9,492,314 B2
APPLICATION NO. : 12/641795
DATED : November 15, 2016
INVENTOR(S) : Michael P. Richardson Page 1 of 1

It is certified that error appears in the above-identified patent and that said Letters Patent is hereby corrected as shown below:

In the Claims

Column 9, Lines 5-7 of Claim 1, replace:
"fluid, a cooling fluid, or both;
a heating fluid and a cooling fluid and comprising a fluid
supply;"

With:
--fluid, a cooling fluid, or both a heating fluid and a cooling fluid and comprising a fluid supply;--

Signed and Sealed this
Fourteenth Day of November, 2017

Joseph Matal
*Performing the Functions and Duties of the
Under Secretary of Commerce for Intellectual Property and
Director of the United States Patent and Trademark Office*